(12) United States Patent
Harrison et al.

(10) Patent No.: US 9,073,754 B2
(45) Date of Patent: Jul. 7, 2015

(54) SYSTEMS, METHODS, AND COMPOSITIONS INVOLVING CHLORINE DIOXIDE AND ZEOLITE

(75) Inventors: Ken Harrison, Madison, VA (US); Nick Blandford, Charlottesville, VA (US)

(73) Assignee: Dharma IP, LLC, Delray Beach, FL (US)

( * ) Notice: Subject to any disclaimer, the term of this patent is extended or adjusted under 35 U.S.C. 154(b) by 130 days.

(21) Appl. No.: 12/468,125

(22) Filed: May 19, 2009

(65) Prior Publication Data

US 2009/0297629 A1    Dec. 3, 2009

Related U.S. Application Data

(60) Provisional application No. 61/057,382, filed on May 30, 2008.

(51) Int. Cl.
*C01B 11/02* (2006.01)

(52) U.S. Cl.
CPC .................................... *C01B 11/022* (2013.01)

(58) Field of Classification Search
CPC .................. C01B 11/022; C01B 33/28; C01B 2210/0018; C01B 2210/0007; C01B 13/027; C01B 33/2807; B01J 20/165; B01J 20/3238; B01J 20/18
See application file for complete search history.

(56) References Cited

U.S. PATENT DOCUMENTS

| | | | |
|---|---|---|---|
| 4,319,057 A | 3/1982 | Kiser | |
| 5,165,910 A | 11/1992 | Oikawa | |
| 5,380,517 A | 1/1995 | Sokol | |
| 5,403,828 A | 4/1995 | Lewis | |
| 5,741,757 A | 4/1998 | Cooper | |
| 5,814,312 A | 9/1998 | Reich | |
| 5,840,268 A | 11/1998 | Ikegami | |
| RE36,064 E | 1/1999 | Davidson | |
| 5,855,861 A | 1/1999 | Lee | |
| 6,033,641 A * | 3/2000 | Hall et al. | 423/239.2 |
| 6,046,243 A | 4/2000 | Wellinghoff | |
| 6,051,135 A | 4/2000 | Lee | |
| 6,131,774 A | 10/2000 | Thomas | |
| 6,238,643 B1 | 5/2001 | Thangaraj | |
| 6,358,935 B1 | 3/2002 | Beck | |
| 6,468,479 B1 | 10/2002 | Mason | |
| 6,582,682 B2 | 6/2003 | Stier | |
| 6,689,378 B1 | 2/2004 | Sun | |
| 7,229,647 B2 | 6/2007 | Lee | |
| 7,416,326 B2 | 8/2008 | Sakata | |
| 7,467,633 B2 | 12/2008 | Smith | |
| 7,678,388 B2 | 3/2010 | Mason | |
| 2002/0061822 A1 | 5/2002 | Kostansek | |
| 2002/0192340 A1 | 12/2002 | Swart | |
| 2003/0133833 A1* | 7/2003 | Thomas et al. | 422/29 |
| 2004/0104127 A1 | 6/2004 | Rojas | |
| 2004/0137202 A1 | 7/2004 | Hamilton | |
| 2004/0175435 A1 | 9/2004 | Beck | |
| 2005/0218054 A1 | 10/2005 | Sakata | |
| 2005/0224750 A1* | 10/2005 | Yang et al. | 252/186.1 |
| 2005/0250649 A1 | 11/2005 | Jacobson | |
| 2005/0272606 A1 | 12/2005 | Manchak | |
| 2006/0006361 A1 | 1/2006 | Callerame | |
| 2006/0039840 A1 | 2/2006 | Chia | |
| 2007/0224233 A1 | 9/2007 | Maekawa | |
| 2008/0023668 A1 | 1/2008 | Callerame | |
| 2008/0181973 A1 | 7/2008 | Lee | |
| 2009/0054375 A1 | 2/2009 | Harrison | |
| 2009/0105323 A1 | 4/2009 | Bliss | |
| 2009/0298689 A1 | 12/2009 | Iverson | |

FOREIGN PATENT DOCUMENTS

| | | | |
|---|---|---|---|
| CA | 2680934 | | 9/2008 |
| CN | 1166362 | | 12/1997 |
| CN | 1820607 | | 8/2006 |
| EP | 11925858 | | 4/2002 |
| JP | 60-075329 | | 4/1985 |
| JP | 61-234930 | | 10/1986 |
| JP | 91000979 B | * | 1/1991 |
| JP | H0300979 | | 1/1991 |
| JP | H06107971 | | 4/1994 |
| JP | 2532887 | | 6/1996 |
| JP | 2532887 B2 | * | 9/1996 |
| JP | 09-071502 | | 3/1997 |
| JP | 10-030091 | | 2/1998 |
| JP | 11506308 | | 6/1999 |
| JP | 2003326277 | | 11/2003 |

(Continued)

OTHER PUBLICATIONS

Sircar et al. Gas Separation by Zeolites, included in Handbook of Zeolite Science and Technology as Chapter 22 (CRC Press 2003).*
Sugihara et al. Effect of Exchanged Cations upon the Electron Spin Resonance Hyperfine Splitting of Chlorine Dioxide Adsorbed on X-Type Zeolites. J. Phys. Chem. 1977;81(7):669-673.*
Apolonatos, G. "Gas Adsorption with Molecular Sieve Zeolites" Thesis (Univ. of Ottawa) 1990.*
Payra et al. "Zeolites: A Primer" in Handbook of Zeolite Science and Technology, Chapter 1 (CRC Press 2003).*

(Continued)

*Primary Examiner* — Bethany Barham
*Assistant Examiner* — Peter Anthopolos
(74) *Attorney, Agent, or Firm* — Michael Haynes PLC; Michael N. Haynes

(57) ABSTRACT

Certain exemplary embodiments can provide one or more systems, machines, devices, manufactures, compositions of matter, and/or methods for, activities that can comprise, creating a composition comprising chlorine dioxide adsorbed in a zeolite, and/or releasing at least a portion of the chlorine dioxide from the composition, the released chlorine dioxide potentially useful for disinfection, decolorization, mildew control, and/or odor control.

12 Claims, 5 Drawing Sheets

(56) References Cited

FOREIGN PATENT DOCUMENTS

| JP | 2006-2044 | 8/2006 |
|---|---|---|
| JP | 2006-204445 | 8/2006 |
| JP | 2007217239 A * | 8/2007 |
| KR | 20020009544 | 2/2002 |
| WO | WO9624388 | 8/1996 |
| WO | WO9641526 | 12/1996 |
| WO | WO00/12137 | 3/2000 |
| WO | WO0158265 | 8/2001 |
| WO | WO03/093170 | 11/2003 |

OTHER PUBLICATIONS

Xing, Abstract of "Study on Controlled Release Chlorine Dioxide Microcapsules", 2004, 1672-1098, Anhui Ligong Daxue Xuebao Bianjibu, 24 (2), 52-55, People's Republic of China.
Coope, "Electron Spin Resonance Study of C102 and C12- Adsorbed on Zeolites", 1971, Molecular Physics, 21(6), 1043-1055.
Pietrzak, "Preferred Rotation of C102 adsorbed on CaX and Synthetic Zeiolites", Jun. 30, 1972, Molecular Physic, 24(4), 909-911.
Shimokoshi, "Electron Spin Resonance Study of Chlorine Dioxide Adsorbed on the Alkali-Cation-Exchanged X-Type Zeolites", 1974, Journal of Physical Chemistry, 78(17), 1770-1771.
Sugihara, "Effect of Exchanged Cations upon the Electron Spin Resonance Hyperfine Splitting of Chlorine Dioxide Adsorbed on X-Type Zeiolites", 1977, Journal of Physical Chemistry, 87(7), 669-673.
Wimmer, "Cyclodextrins—From Ullmann's Encyclopedia of Industrial Chemistry", Jan. 15, 2003, 9 page(s), Wiley-VCH Verlag GmbH & Co. KGaA, Weinheim.
Hedges, "Industrial Applications of Cyclodextrins", May 27, 1998, 10 pages, Chem. Rev. 1998, 2035-2044.
Masschelein, "Preparation of Pure Chlorine Dioxide", Jun. 1, 1967, 6 page(s), I&EC Product Research and Developement, vol. 6 No. 2.
Tchobanoblous & Burton, "Wastewater Engineering: Treatment, Disposal, and Reuse, 3rd Edition", Jan. 1, 1991, p. 50-51, Metcalf & Eddy, Inc. McGraw-Hill, Inc.
Bio-Cide International, Inc., "Summary of Antimicrobial Efficacy", Jan. 1, 2008, 1 page, http://www.bio-cide.com/prod_oxine_oxine_ad_microbial.htm.
Copes, "Activity of Chlorine Dioxide in a Solution of Ions and pH Against *Thielaviopsis basicola and Fusarium oxysporum*", Jan. 1, 2004, 7 pages, Plant Disease vol. 88 No. 2; American Phytopathological Society.
Franson (Managing Editor), "Standard Methods for the Examination of Water and Wastewater, 20th Ed.", Jan. 1, 1998, pp. 4-73-4-79, APHA, Washington D.C.
Mebalds, "Using Ultra Violet Radiation and Chlorine Dioxide to Control Fungal Plant Pathogens in Water", Jan. 1, 1996, 2 pages, The Nursery Papers, Issue 1996-005.
OxyChem, "Laboratory Preparations of Chlorine Dioxide Solutions-Technical Data Sheet", Dec. 22, 2006, 4 pages.

Chemical Abstracts Service, "Chemical Abstracts, vol. 49, No. 5, p. 5213", Mar. 10, 1955, The American Chemical Society.
Chemical Abstracts Service, "Chemical Abstracts, vol. 51, No. 21, p. 16609", Nov. 10, 1957, The American Chemical Society.
Sigma-Aldrich, "Material Safety Data Sheet for Molecular Sieves 4A Powder", May 16, 2008, 5 page(s), SIAL—688363; www.sigma-aldrich.com.
Wang Yufeng, Xing Honglong, "A Study on Sustained Release Chlorine Dioxide Microcapsules", Jun. 1, 2004, 9 page(s) with translation, Journal of Anhui University of Science and Technology (Natural Science) vol. 24 No. 2.
Mosby's Dental Dictionary, ""Disinfectant"", Jan. 1, 2008, 4 pages, 2nd Ed., 2008, Elsevier.
Suslow, "Postharvest Chlorination: Basic Properties and Key Points for Effective Disinfection", Jan. 1, 1997, 8 pages, University of California Division of Agriculture and Natural Resources, Pub. 8003, by Regents of the University of Californnia.
United States Environmental Protection Agency, "Anthrax spore decontamination using chlorine dioxide", Jul. 1, 2007, 4 pages, U.S. EPA; Pesticides: Topical and Chemical Fact Sheets.
Gates, "The Chlorine Dioxide Handbook—Water Disinfection Series", Jan. 1, 1998, p. 8, American Water Works Association, Denver, CO.
Derwent, "Soil microbicidal and nematocidal composition having low toxicity—consists mainly of stabilised chlorine dioxide, supplying oxygen to roots of plants", Mar. 18, 1997, 1 page.
Derwent, "Soil reformation for disinfection—comprises penetrating dilute solution containing chlorine dioxide into soil and giving soil useful microbes to soil", Feb. 3, 1998, 1 page.
Kaczur, "Chlorine Oxygen Acids and Salts: Chlorous Acid, Chlorites, and Chlorine Dioxide. Encyclopedia of Chemical Technology.", Jan. 1, 1993, 33 pages, Wiley.
Ames, "Zeolite Cation Selectivity", Jan. 1, 1965, p. 325-333, The Canadian Mineralogist 8.3 (1965).
Click, "Techniques of Histo- and Cytochemistry", 1949, 470 pages, Interscience Publishers, Inc.; available online at http://www.archive.org/stream/techniqueso fhist031071mbp/techniquesofhist031071mbp_djvu.txt.
Grandcircuitinc.com, "Overview of Chlorine Dioxide (C1O2)", Aug. 31, 2001, 17 pages, http://www.grandcircuitinc.com/Howard%20Alliger%20-%20An%20Overall%20View%20C1O2.pdf.
Gray, "The Microtomist's Formulary and Guide", 1954, 1096 pages, The Blakiston Company, Inc.; available online at http://www.archive.org/stream/microtomistsform00gray/microtomistsform00gray_djvu.txt.
Kroshcwitz, editor, "Kirk-Othmer Encyclopedia of Chemical Technology, 4th Ed. vol. 5", 1993, p. 972, John Wiley & Sons, Inc., New York, NY.
Richards, A. Glenn, and Frances H. Korda. "Studies on arthropod cuticle. II. Electron microscope studies of extracted cuticle." The Biological Bulletin 94.3 (1948):212-235.

* cited by examiner

| Zeolite | ClO2 adsorption from gas phase | | | ClO2 adsorption from aqueous soln (% by wt.) |
| --- | --- | --- | --- | --- |
| | Amount of ClO2 adsorbed (% by wt.) | ClO2 recovered by extraction | | |
| | | (% by wt.) | eluent | |
| 3A beads (untreated) | NT | 1.9 | water | NT |
| 4A powder, boric acid washed | 20.1 | 10.6 | 1% citric | ND |
| 4A beads, citric acid washed | 17.1 | 14.8 | 1% citric | ND |
| 5A beads (untreated) | NT | 2.6 | water | NT |
| 13X powder, boric acid washed | 25.1 | 20.4 | 1% citric | ND |
| 13X pellets, citric acid washed | 18.9 | 19 | 1% citric | ND |
| CBV 901 | 2.3 | NT | NT | 1.2 |
| CBV 28014 | 10.9 | 9.1 | water | 15.2 |
| | | | | 13.3$^{SL}$ |
| calcined CBV 28014 | 7.0 | 4.9 | water | 15.8 |
| Extrudate CBV 28014CY (1.6) | 9.1 | 7.2 | water | 12.3 |
| CBV 5524G | 8.4 | 3 | water | 9.3 |
| calcined CBV 5524G | NT | NT | NT | 7.6 |

ND = None detected
NT = Not tested
SL = Slurry method, i.e., gaseous ClO2 bubbled through a water slurry of the zeolite.

FIG. 3

SYSTEMS, METHODS, AND COMPOSITIONS INVOLVING CHLORINE DIOXIDE AND ZEOLITE

CROSS-REFERENCES TO RELATED APPLICATIONS

This application claims priority to U.S. Provisional Patent Application 61/057,382, filed 30 May 2008.

BRIEF DESCRIPTION OF THE DRAWINGS

A wide variety of potential practical and useful embodiments will be more readily understood through the following detailed description of certain exemplary embodiments, with reference to the accompanying exemplary drawings in which:

FIG. 3 is a table listing experimental results involving certain exemplary embodiments;

DETAILED DESCRIPTION

Chlorine dioxide ("ClO2") can be an excellent disinfectant, and/or can be effective against a wide range of organisms. For example, ClO2 can provide excellent control of viruses, bacteria, and/or the protozoan parasites *Giardia, Cryptosporidium*, and/or amoeba *Naegleria gruberi* and/or their cysts.

In addition to disinfection, ClO2 can have other beneficial uses in water treatment, such as color, taste, and/or odor control, and/or removal of iron and/or manganese. There are also important uses outside of water treatment, such as bleaching pulp and/or paper (its largest commercial use), disinfection of surfaces, and/or sanitization/preservation of fruits and/or vegetables.

ClO2 can present certain challenges, which can stem largely from its inherent physical and/or chemical instability. ClO2 in pure form is a gaseous compound under normal conditions. As a gas, it can be sensitive to chemical decomposition, exploding at higher concentrations and/or when compressed. Thus, pure condensed phase (liquid or solid) ClO2 is typically very sensitive, reacting rapidly, often violently, under any but the most carefully controlled conditions, and even then typically is unpredictable.

Because ClO2 can be highly soluble in water, ClO2 can be used as a solution of ClO2 gas dissolved in water. However, the gaseous nature of ClO2 means that it can be volatile, thus ClO2 tends to evaporate rapidly from solutions when open to the atmosphere (physical instability). This tendency can limit the practically useful concentrations of ClO2 solutions. With concentrated solutions, this rapid evaporation can generate gaseous ClO2 concentrations that can present an unpleasantly strong odor and/or can pose an inhalation hazard to users. A closed container of the solution can quickly attain a concentration in the headspace of the container that is in equilibrium with the concentration in the solution. A high concentration solution can have an equilibrium headspace concentration that exceeds the explosive limits in air (considered to be about 10% by weight in air).

For these and other reasons, virtually all commercial applications to date have required that ClO2 be generated at the point of use to deal with these challenges. However, on-site generation also can have significant draw-backs, particularly in the operational aspects of the equipment and/or the need to handle and/or store hazardous precursor chemicals. It can be desirable to have additional forms of ready-made ClO2.

Certain exemplary embodiments can provide one or more systems, machines, devices, manufactures, compositions of matter, and/or methods for, activities that can comprise, creating a composition comprising chlorine dioxide adsorbed in a zeolite, and/or releasing at least a portion of the chlorine dioxide from the composition, the released chlorine dioxide potentially useful for disinfection, decolorization, mildew control, and/or odor control.

Figure 1:
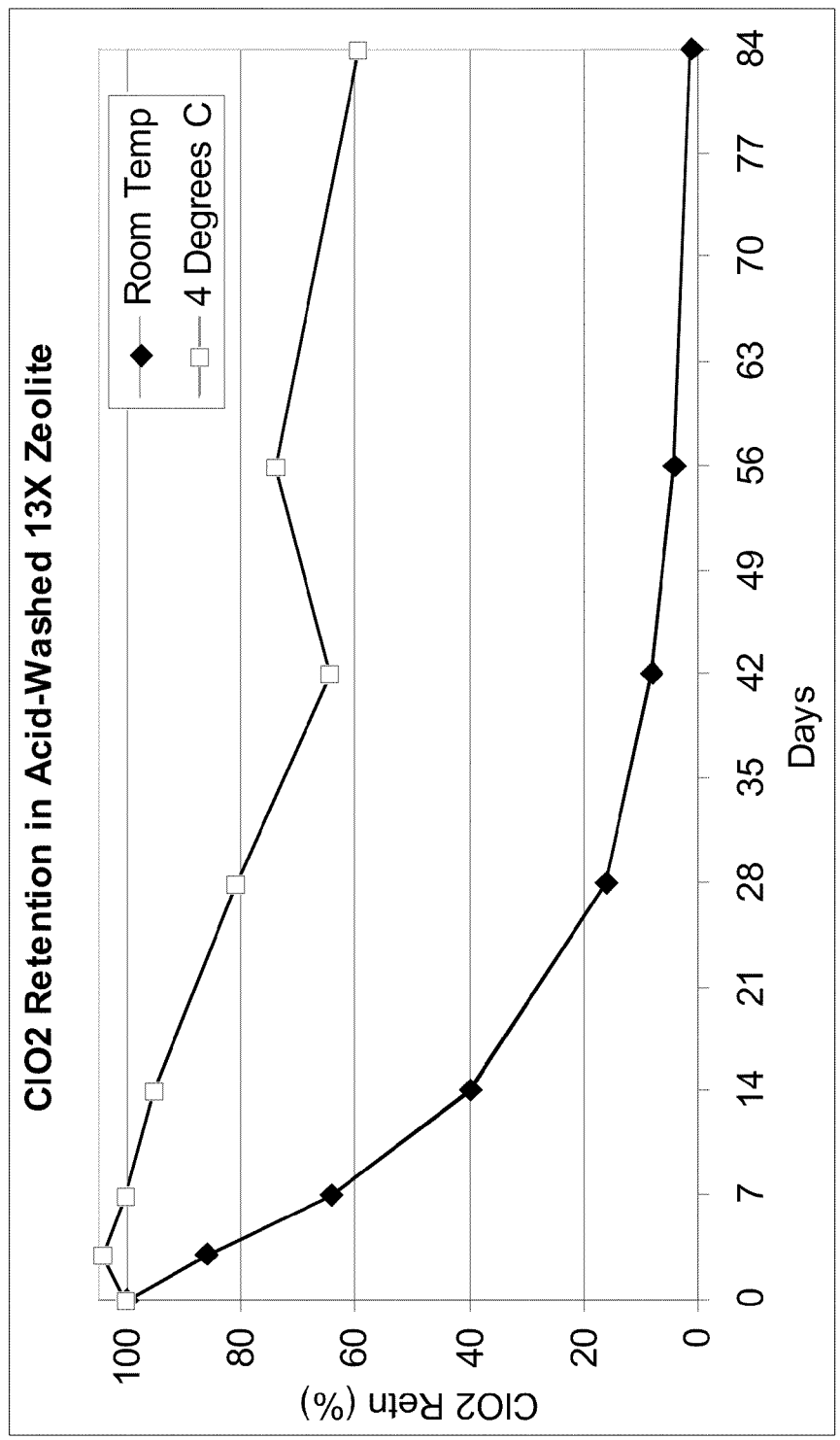
FIG. 1 is a chart of experimental results involving certain exemplary embodiments.
Figure 2:
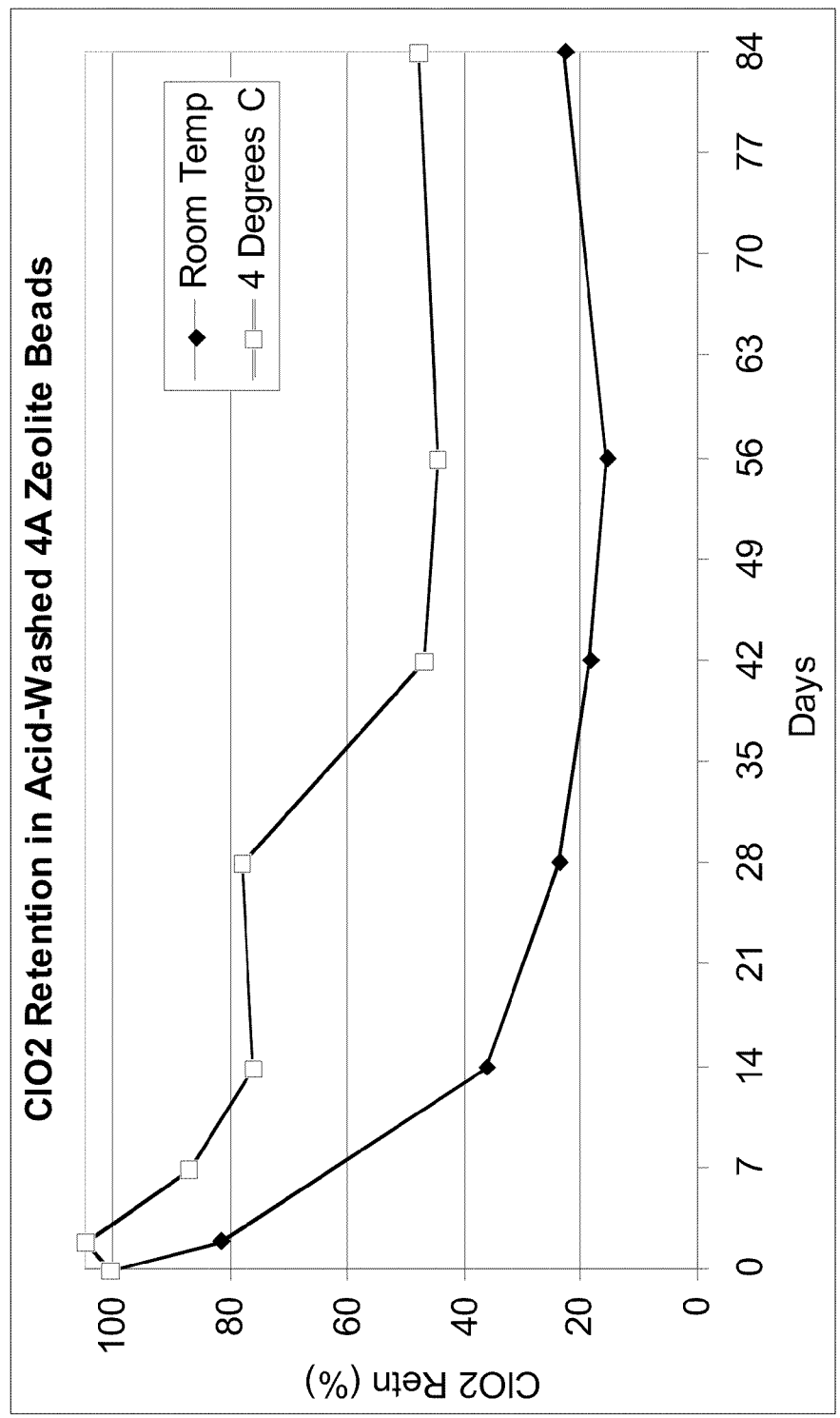
FIG. 2 is a chart of experimental results involving certain exemplary embodiments.

We have unexpectedly discovered that, by passing a dry stream of gaseous chlorine dioxide (ClO2) in nitrogen, through a column of zeolite, which can be in the form of, for example, extruded pellets and/or powder, the zeolite can capture and/or concentrate the ClO2. Because of the volatile and reactive nature of ClO2, it is surprising that this complex is stable, in part because zeolites are considered to be incompatible with strong oxidizing agents. In the absence of a solvent or diluent in the conventional sense, if ClO2 adsorbed in, on, and/or by zeolite is viewed as a condensed phase occupying the channels in the zeolite structure, the absence of violent, or even controlled but rapid, destruction of all the adsorbed ClO2 represents (at least relative) stability. This stability can be measured by the ability to recover ClO2 from the zeolite. FIGS. 1 and 2 present qualitative measurements (e.g., "ClO2 recovered by extraction/(% by wt.)") of the improved stability we have discovered. That is, the level of ClO2 that can be adsorbed in, on, and/or by the zeolite represents an unpredictably high concentration for a stable composition. Moreover, the ClO2 can subsequently be released from the zeolite by exposing it to air or water.

Due to its high volatility and reactivity, ClO2 is typically not transported or stored, but is generated at the site and time of use. Adsorption of ClO2 in zeolite has not been reported. Thus, this discovery might represent an important new capability for the transportation, storage and delivery of ClO2. The discovery includes the complexes between ClO2 and various varieties of zeolite, methods of preparing the complexes, and methods of using the complexes. Note that the use of the term "complex" herein is not meant to assert any specific molar ratio relationship, nor any specific type of chemical interaction between the zeolite and the adsorbed ClO2.

In certain exemplary embodiments, the ClO2 to be incorporated into the zeolite complex can be obtained from a ClO2 generator or from a solution of ClO2 in water. A suitable source can be essentially any source that will allow a stream of gaseous ClO2 diluted in an essentially inert secondary gas to be formed. The secondary gas generally should have a relatively low affinity for the zeolite. For example, we have found nitrogen to be an acceptable secondary gas. The gaseous mixture can be dried before it contacts the zeolite (which also can be dried before use by heating, as is known in the art). We have passed the gas stream through a column of anhydrous calcium sulfate (e.g., Drierite™) desiccant to dry it. Thereafter the gas stream can be passed through the column containing the zeolite.

In certain exemplary embodiments, this step of drying the ClO2 gas stream before it contacts the zeolite can be particularly important when the zeolite is a hydrophilic type (such as those having a relatively low silicon-to-aluminum ratio ("SAR") in their composition; the A and X type zeolites used herein are hydrophilic.) Hydrophilic zeolites can preferentially adsorb water vapor if it is present in the gas stream. It also can be important to assure that the zeolite is essentially free of moisture before subjecting it to the ClO2 treatment, else the ClO2 might not displace the moisture (zeolites can be dried prior to use by heating, as is known in the art).

In a typical set-up, a 500 ml flask substantially full of approximately 4000 ppm ClO2 solution can be sparged with nitrogen, such as at a flowrate of from less than approximately 72 ml/min to approximately 200 ml/min. The nitrogen gas stream then can contain ClO2. This gas stream can be directed via flexible tubing into a chromatography column packed with a sufficient amount of Drierite to dry the gas stream to the extent that indicating Drierite (blue when dry, and pink when saturated with moisture) at the downstream end of the column shows no color change. It can be convenient to include at least some color-indicating Drierite at the downstream end of the column to assure that it still has moisture-capturing capability through the end of the process. Next the dried gas stream can be directed through a column of the zeolite (conveniently approximately 10 g), via flexible tubing. Alternatively the zeolite can occupy a downstream section of the same chromatography column as the Drierite, the two materials being separated by a porous barrier such as paper to prevent commingling. The gas stream finally can pass through a small orifice before passing into the open air or bubbling through a vessel containing a liquid such as, for example, water (potentially in order to capture ClO2 that was not captured by the zeolite) or mineral oil. The small orifice can restrict backflow of air into the apparatus, and/or can be used to help raise the pressure inside the apparatus by restricting out-flow. Pressure inside the apparatus (originating from the nitrogen source) can be allowed to build up within the chamber containing the zeolite, such as up to approximately 3 psi (gauge). The positive pressure can increase the amount of ClO2 that can be concentrated into the zeolite and/or the speed with which it can be adsorbed.

As an alternative approach to preparing the zeolite complex, early indications are that zeolite can also adsorb ClO2 from certain non-aqueous solvents. ClO2 can be dissolved in a solvent such as heptane for example, by bubbling a gas stream containing ClO2 through the heptane and/or by extraction of ClO2 from an aqueous solution into heptane. Adding dry zeolite to the non-aqueous ClO2 solution (which also can be dry) can result in decolorization of the yellow color of ClO2 from the solvent. The zeolite then can be isolated from the solvent (by decanting and/or blotting with absorbent paper). The isolated zeolite then can be immersed in water. The ClO2 can be released into the water, as indicated by yellow color and/or ClO2 indicator test strips. This approach might have practical advantages for making the complex over the direct gas-phase absorption technique. One possible improvement on this approach might be to use a more volatile non-aqueous solvent to permit easier and/or more complete removal of solvent from the zeolite complex. Alternatively, a relatively non-volatile hydrophobic solvent might be used as a barrier to protect the zeolite complex from loss of ClO2 through displacement by air components (including humidity).

It has been observed that the hydrophobic zeolites, such as those we have tested from Zeolyst International, of Conshohocken, Pa., can adsorb ClO2 from aqueous solutions (although this does not appear to be true with the hydrophilic zeolites of the A-type and the X-type.) This adsorption appears to be an equilibrium or equilibrium-like situation, in which the zeolite adsorbs only a portion of the ClO2 from solution, leaving the remainder in solution. As the treating ClO2 solution concentration becomes greater, the amount of ClO2 adsorbed can become greater (up to the limiting capacity of the zeolite), but with always a portion of the total ClO2 remaining in solution. This solution-phase treatment can be accomplished by adding the zeolite to an aqueous solution of ClO2. Alternatively, the zeolite can be mixed with pure water (or a ClO2 solution), then subsequently a gas stream containing ClO2 can be bubbled through the mixture, so that additional ClO2 can be captured by the water/zeolite combination.

In certain exemplary embodiments, this latter approach can have the advantage that, practically speaking, a higher net quantity of ClO2 can be safely accumulated in a given volume. In practice, the limiting usable ClO2 solution concentration is usually determined by safety considerations. For example, an aqueous solution concentration of 8000 ppm is approximately the highest concentration whose equilibrium headspace gas-phase concentration of ClO2 does not exceed the 10% level at room temperature. (It is generally understood that gas-phase concentrations of >10% ClO2 have the potential for explosive reaction, whereas ≤10% do not pose this risk.) If a zeolite capable of adsorbing ClO2 from solution is added to an 8000 ppm ClO2 solution, the zeolite can adsorb some fraction of the ClO2, such that the concentration in solution drops below the 8000 ppm level. By bubbling additional ClO2 into the zeolite/water system, the safe ClO2 content of the system can be increased until the concentration in solution again reaches, for example, 8000 ppm, but with a potentially much greater net ClO2 content in the system than in a simple 8000 ppm aqueous solution of the same volume. (This assumes that the zeolite is totally immersed in the solution, and that only the solution is in contact with the headspace.)

The latter approach can provide a potentially valuable ClO2 vehicle. Bubbling a ClO2 gas stream through a water/zeolite mixture can be a more practical process than the gas-phase treatment process. Also, the water/zeolite mixture can be more practical for end use. In particular, if a powdered zeolite is used, the water/zeolite mixture can be a fluid slurry that can be a more convenient form for end use than the dry zeolite powder.

In certain exemplary embodiments, ClO2 can be recovered from the zeolite complex by placing it into water. The zeolite itself typically is totally insoluble in water. The ClO2 can transfer from the zeolite directly into aqueous solution. If approximately 1 g of zeolite complex is added to approximately 100 g of water and swirled gently, the amount of ClO2 released into the water appears to reach nearly a maximum after approximately 1 hour of swirling. The ClO2 concentration in the water might continue to rise thereafter, or it might decline, presumably depending on the initial concentration in the zeolite. Declining subsequent concentrations of ClO2 might be at least in part due to decomposition of the ClO2 caused by the alkaline pH imposed on the water by some types of zeolite. It is expected that the stability of the aqueous extract, especially longer-term stability, can be enhanced by including an amount of an acid with which the ClO2 is compatible in the water, such as acetic and/or citric acid, sufficient to keep the water at a pH appropriate to the required stability. For example, we have found that for some zeolite/ClO2 complexes the complexed zeolite is more soluble in an acid extract than is the corresponding pure zeolite used as a control. For example, when up to 1 g of 4 A powder or 13× powder complexed with ClO2 is extracted with about 100 g of 1% citric acid solution, all or virtually all of the powder becomes dissolved, resulting in a clear solution. When up to 1 g of 4 A powder or 13× powder complexed with ClO2 is extracted with about 100 g of plain deionized water, most or all of the powder remains undissolved, as judged by visual inspection.

By the same token, when one attempts to extract the ClO2 from hydrophobic zeolites with water (for analysis or utilization), a larger quantity of water can be required (either as a single large-volume extract or multiple smaller extracts) to essentially completely remove the ClO2 as compared to extraction of the hydrophilic zeolites.

It is noted above that the stability of the extract solution might be negatively impacted by the alkalinity imparted to the extract by some zeolites, and that this can be mitigated by using an acidic extraction solution. It has been discovered that, in certain exemplary embodiments, this alkalinity effect can be mitigated by pre-treatment of such zeolites with appropriate mild acid before the ClO2 treatment step. Beads of 4 A and pellets of 13× were washed repeatedly with 1% citric acid solution until the wash pH remained acidic, then they were rinsed with plain water; powders of the same zeolites were similarly washed with 1% boric acid then rinsed. It has been discovered that this acid pre-treatment appears to increase the storage stability of the adsorbed ClO2, as well as modestly increasing the ClO2 adsorbing capacity of the zeolite and/or increasing the extraction efficiency.

The following synthetic zeolites have been tested to date, using the 4-8 mesh size beads thereof: 3 A, 4 A, and 5 A. These widely used designations indicate the pore sizes of the different types, in angstrom units. All three zeolites have been shown to adsorb significant amounts of ClO2. These zeolites are available in other macro-scale sizes and shapes besides the 4-8 mesh beads. These macro forms are fabricated from the powder form of the zeolite that is typically obtained when it is initially synthesized; the powder form itself is commercially available as well. There are also natural mineral zeolites with a similar range of pore sizes and similar chemical composition and structure around the pores. Thus it is believed that any zeolite with adequate pore size will adsorb ClO2 to some degree. It is expected that different zeolite complexes may be advantageous for different applications due to differences in economics and physical properties (ease of formation, ultimate ClO2 capacity, release rates, etc.).

In addition to the identified zeolites in bead form, we subsequently tested the powder form of 4 A. We also tested 13× in powder and extruded pellet form. Both types, in both forms, were additionally tested with acid pre-treatment. (All A and X types/forms were obtained from SigmaAldrich, of St. Louis, Mo.) From Zeolyst International we obtained and tested CBV 901 (a 'Y' type zeolite, tested as the powder), CBV 5524G (a 'ZSM-5' type zeolite, tested as the powder) and CBV 28014 (also 'ZSM-5' type, tested as powder and "extrudate" pellets (pellets having the suffix 'CY (1.6)')).

In certain exemplary embodiments, zeolites can have a negative charge associated with each aluminum atom in the framework. They typically must have cationic (positively charged) counterions to balance these negative charge sites. CBV 901 is supplied in a form in which the cation is identified as "hydrogen". CBV 5524G and CBV 28014 are supplied with ammonium (NH4+) as the cation. Using a supplier-prescribed calcination process, portions of each of the latter were converted in our lab to the "hydrogen" cation form. We believed that there could be differences in ClO2 capacity and/or stability between the ammonium and hydrogen forms of these zeolites. Every one of the zeolites we tested adsorbed a significant amount of ClO2 via gas-phase treatment.

Initial indications are that the 4 A zeolite accepts ClO2 to the greatest degree of the three A-type zeolites tested so far. In one case, the amount of ClO2 recovered from a sample of 4 A zeolite represented approximately 9.1% by weight of the sample, or approximately 91,000 ppm. On a volume basis, this represents approximately 65 g of ClO2 per liter. (The 4 A zeolite beads have a bulk density of approximately 710 g/L.) This concentration would not be stable in the case of free gaseous ClO2 since concentrations in air in excess of approximately 10% are explosive, and compression of ClO2 also leads to explosion. Such a concentration of ClO2 in water would represent a significantly hazardous material due to rapid off-gassing, spill and splash potential, and possibly an explosion hazard of the liquid and/or the headspace gas in equilibrium with it inside a closed container. However the zeolite complex shows no sign of representing a hazard other than possibly rapid off-gassing of high-ClO2 content systems.

FIG. 3 presents a table identifying the best ClO2 loadings observed to date, as a weight percent of the post-treatment zeolite weight. It may be possible to increase these loadings by exposure of the zeolites to ClO2 at higher concentration and/or at elevated pressure and/or for longer periods of time.

As an extension of the possible physical forms of the zeolite/ClO2 complexes, we have found that a sample of the 4 A bead complex could be crushed and tableted, and that the 4 A powder complex could be tableted directly, using a tablet press. It is believed that such tableted complex, or tablets formed from zeolite/ClO2 complex combined with other components, could have important practical applications.

Figure 4:
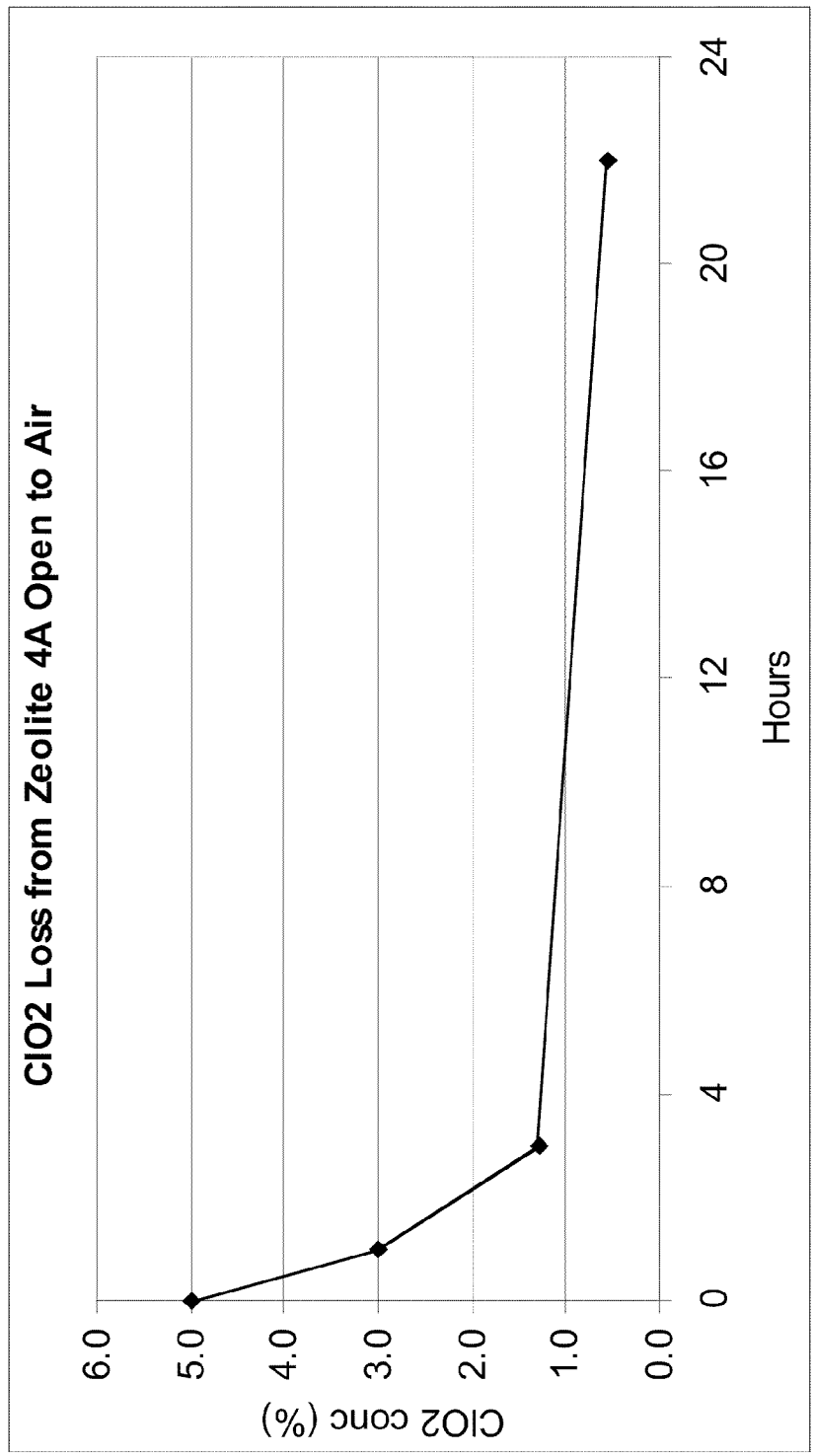
FIG. 4 is a chart of experimental results involving certain exemplary embodiments.
Figure 5:
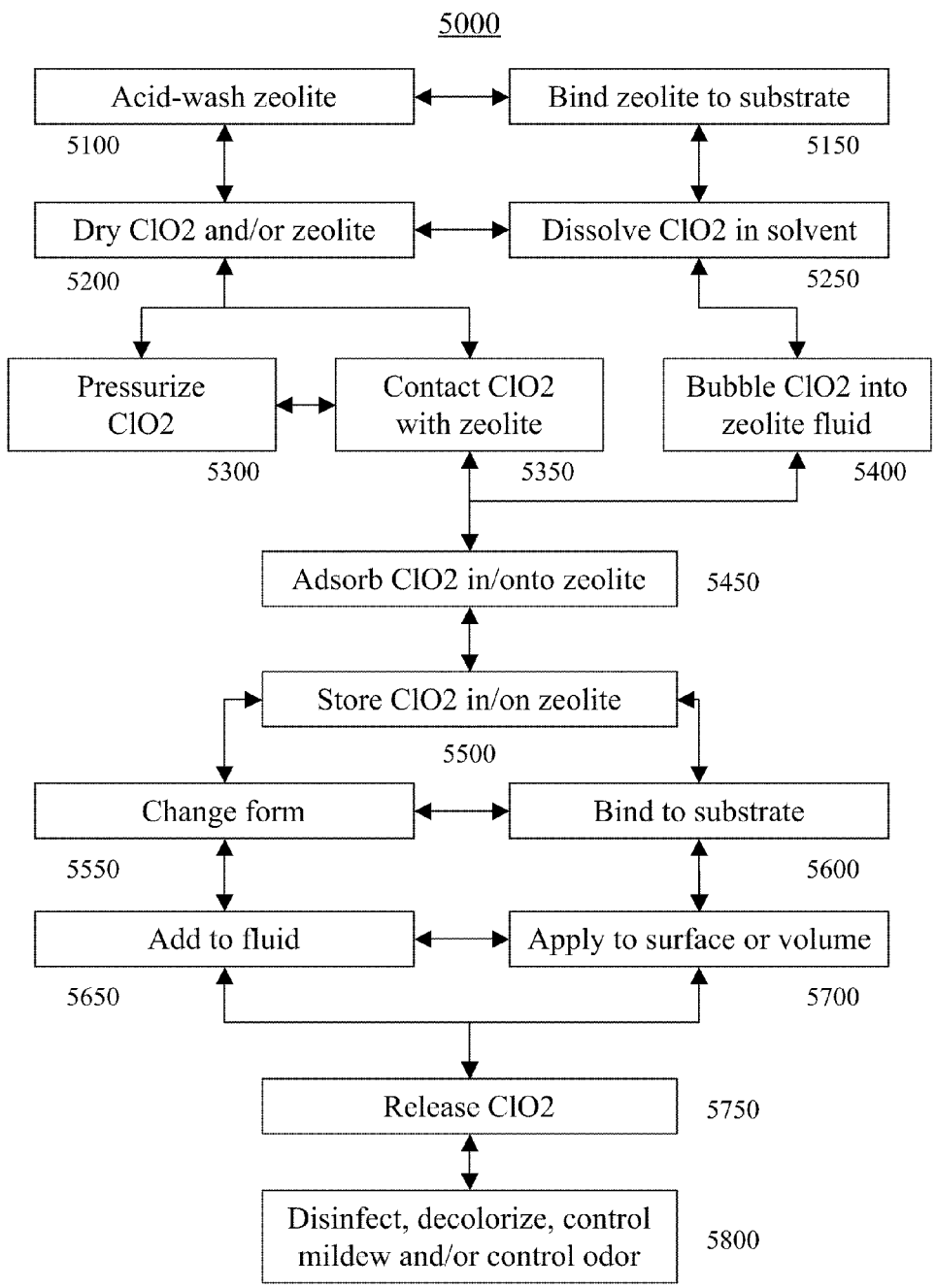
FIG. 5 is a flowchart of an exemplary embodiment of a method.

In certain exemplary embodiments, the ClO2 impregnated zeolite can lose ClO2 into the open air fairly quickly. FIG. 4 presents a graph showing the rate of loss from an exemplary sample of ClO2 impregnated beads arranged in a single layer, in an open beaker, in a well-ventilated area. It is not yet clear whether ClO2 is lost from the zeolite through displacement by air molecules or by airborne moisture. It has been observed that the headspace above a zeolite complex containing a moderate ClO2 concentration (≤approximately 3.7%), placed in a closed container under low-humidity conditions, contained little gaseous ClO2, at least within a day or two. Other containers of moderate concentration zeolite complex packaged under conditions of uncertain humidity eventually developed substantial ClO2 concentrations, as indicated by odor. High concentration (approximately 9.1%) complex attained a significant headspace concentration quickly after packaging it, under somewhat humid conditions, reaching a maximum of almost approximately 1% in the air. These observations suggest that at least some displacement may be accomplished by moisture from the air, though there may tend to be some loss of ClO2, most conspicuous with high-concentration complex, through simple exchange with air molecules.

In certain exemplary embodiments, the zeolite complex can be added directly into the water which is desired to be treated. Alternatively, the zeolite complex can be added to a quantity of water to form a solution which could then be used for treating surfaces, waters or other materials. Solutions of ClO2 prepared by adding the complex to water, either the water to be treated or an intermediate solution, can be used for any purpose known in the art for which a simple aqueous solution of comparable ClO2 concentration would be used, insofar as this purpose is compatible with the presence of the zeolite, or allows for the zeolite to be separated from the solution (by filtration, settling, etc.). These uses include, but would not be limited to, disinfection and/or deodorization and/or decolorization of: drinking water, waste water, recreational water (swimming pools, etc.), industrial reuse water, agricultural irrigation water, as well as surfaces, including living tissues (topical applications, such as via creams, gels, foams, sprays, bandages, and/or patches, etc.) and foods (produce, meats) as well as inanimate surfaces.

Certain exemplary zeolite complexes can experience a slow release of ClO2 gas directly into the air. Conditions can be selected such that the concentration level of the ClO2 released into the air is low enough to be safe but at a high enough concentration to be efficacious for disinfection and/or odor control in the air, and/or disinfection of surfaces or materials in contact with the air. As mentioned above, this release might be at least partially triggered by atmospheric moisture (humidity). This can be desirable in cases where the need for treatment correlates with humidity, as in control of mildew and its odors. In general, this method can be used for essentially any purpose known in the art for gaseous ClO2 in air, within the range of concentrations which can be thus attained.

It can also be envisioned that certain exemplary zeolite complexes can release ClO2 directly, or via the gas phase, or via moisture which is present, into other substances. For example, the solid might be admixed with such substances, as by mixing powdered or granular zeolite complex with these other substances in powdered or granular form. Or the zeolite complex might be applied to a surface, such as skin or other material, either by "rubbing in" a sufficiently fine powder of the complex, or by holding the solid complex against the surface mechanically, as with a patch or bandage. The substance receiving the ClO2 from the complex might do so as a treatment of the substance, or the substance might act as a secondary vehicle for the ClO2.

It is anticipated that certain exemplary zeolite complexes can be bound, via adhesives for example, to another substrate for use in an application where multiple functionality of a particular product is desired, or for ease of exclusion of the zeolite from further involvement in the process. For example, such a complex bound to an insoluble substrate can, upon contact with water, release its ClO2 into solution while the zeolite and the substrate remain as a single solid unit easily removed from the solution or mechanically held in a position where it will not interfere.

Via certain exemplary embodiments, the zeolite complex of ClO2 can be handled safely at room temperature. When added to water to release the ClO2, the zeolite complex need not introduce any other material into solution, since zeolites are insoluble and inert.

It has been observed that different exemplary ClO2 impregnated zeolite beads within the same treatment batch can have very different ClO2 contents. It might be that the processing that converts the powder to beads leads to beads of different ClO2 adsorptivity. Thus it is suspected that the powder form can have the greatest ClO2 capacity for each zeolite type, though it might be less convenient to work with.

FIG. 35 is a flowchart of an exemplary embodiment of a method 5000. At activity 5100, zeolite can be acid washed. At activity 5150, zeolite can be bound to a substrate. At activity 5200, zeolite and/or chlorine dioxide can be dried. At activity 5250, chlorine dioxide can be dissolved in a solvent. At activity 5300, chlorine dioxide can be pressurized. At activity 5350, chlorine dioxide can be contacted with zeolite. At activity 5400, chlorine dioxide can be bubbled into a zeolite fluid, solution, and/or slurry. At activity 5450, chlorine dioxide can be adsorbed and/or absorbed into and/or onto a zeolite. At activity 5500, chlorine dioxide can be stored in and/or on a zeolite. At activity 5550, a form of a composition can be changed, the composition comprising chlorine dioxide adsorbed and/or absorbed onto and/or into a zeolite. At activity 5600, a composition comprising chlorine dioxide adsorbed and/or absorbed onto and/or into a zeolite can be bound to a substrate. At activity 5650, a composition comprising chlorine dioxide adsorbed and/or absorbed onto and/ or into a zeolite, and/or chlorine dioxide released therefrom, can be added to a fluid. At activity 5700, a composition comprising chlorine dioxide adsorbed and/or absorbed onto and/or into a zeolite, and/or chlorine dioxide released therefrom, can be applied to a surface and/or volume. At activity 5750, chlorine dioxide can be released from a composition comprising chlorine dioxide adsorbed and/or absorbed onto and/or into a zeolite. At activity 5800, chlorine dioxide released from a composition comprising chlorine dioxide adsorbed and/or absorbed onto and/or into a zeolite can be used to disinfect, decolorize, control mildew, and/or control odor.

Certain exemplary embodiments can provide a composition comprising chlorine dioxide adsorbed in a zeolite, wherein: said zeolite is a hydrophilic zeolite, said zeolite is a hydrophobic zeolite, said zeolite is an acid pre-treated zeolite, said chlorine dioxide is adsorbed into said zeolite in an amount greater than 10 percent by post-adsorption weight of said zeolite, said chlorine dioxide is adsorbed into said zeolite in an amount greater than 20 percent by post-adsorption weight of said zeolite, said chlorine dioxide is recoverable via extraction from said zeolite in an amount greater than 10 percent by post-adsorption weight of said zeolite, said chlorine dioxide is recoverable via extraction from said zeolite in an amount greater than 15 percent by post-adsorption weight of said zeolite, said chlorine dioxide is recoverable via extraction from said zeolite in an amount greater than 20 percent by post-adsorption weight of said zeolite, said chlorine dioxide is adsorbed from a fluid into said zeolite in an amount greater than 5 percent by post-adsorption weight of said zeolite, said chlorine dioxide is adsorbed from a fluid into said zeolite in an amount greater than 10 percent by post-adsorption weight of said zeolite, and/or said chlorine dioxide is adsorbed from a fluid into said zeolite in an amount greater than 15 percent by post-adsorption weight of said zeolite.

Certain exemplary embodiments can provide a method, comprising: creating a composition comprising chlorine dioxide adsorbed in a zeolite, drying a gaseous stream comprising said chlorine dioxide prior to said creating, drying said zeolite prior to said creating, washing said zeolite in an acid solution prior to said creating, dissolving said chlorine dioxide in a solvent prior to said creating, forming a non-aqueous solution comprising said chlorine dioxide prior to said creating, forming a non-aqueous fluid comprising said zeolite prior to said creating, applying pressure to said chlorine dioxide, adsorbing said chlorine dioxide into said zeolite, adsorbing said chlorine dioxide into said zeolite from a fluid comprising said chlorine dioxide, introducing a gas stream comprising said chlorine dioxide to a fluid comprising said zeolite, bubbling a gas stream comprising said chlorine dioxide into an aqueous slurry comprising said zeolite, and/or extracting at least a portion of said chlorine dioxide from said zeolite.

Certain exemplary embodiments can provide a method, comprising: storing chlorine dioxide in a zeolite, and/or extracting said chlorine dioxide from said zeolite, wherein: said chlorine dioxide is adsorbed in said zeolite, said chlorine dioxide is extracted from a solvent, said zeolite is a hydrophilic zeolite, said zeolite is a hydrophobic zeolite, said zeolite is an A-type zeolite, said zeolite is an X-type zeolite, said zeolite is a 4 A zeolite, said zeolite is a 5 A zeolite, said zeolite is a 13× zeolite, said zeolite is a Y-type zeolite, said zeolite is a ZSM-5 type zeolite, said zeolite is an acid pre-treated zeolite, said chlorine dioxide is adsorbed into said zeolite in an amount greater than 10 percent by post-adsorption weight of said zeolite, said chlorine dioxide is adsorbed into said zeolite in an amount greater than 20 percent by post-adsorption weight of said zeolite, said chlorine dioxide is recoverable via extraction from said zeolite in an amount greater than 10 percent by post-adsorption weight of said zeolite, said chlorine dioxide is recoverable via extraction from said zeolite in an amount greater than 15 percent by post-adsorption weight of said zeolite, said chlorine dioxide is recoverable via extraction from said zeolite in an amount greater than 20 percent by post-adsorption weight of said zeolite, said chlorine dioxide is adsorbed from a fluid into said zeolite in an amount greater than 5 percent by post-adsorption weight of said zeolite, said chlorine dioxide is adsorbed from a fluid into said zeolite in an amount greater than 10 percent by post-adsorption weight of said zeolite, and/or said chlorine dioxide is adsorbed from a fluid into said zeolite in an amount greater than 15 percent by post-adsorption weight of said zeolite.

Certain exemplary embodiments can provide a method, comprising: changing a composition, comprising chlorine dioxide adsorbed in a zeolite, from a first form into a second form, binding said composition to a substrate, adding said composition to water, adding said composition to a fluid, applying said composition to a surface, and/or applying said composition to a volume, wherein: said second form is a powder, said second form is granular, said second form is a tablet, said second form is a gel, said second form is aqueous, said second form is a slurry, and/or said second form is fluidic.

Certain exemplary embodiments can provide a method, comprising: releasing chlorine dioxide from a composition comprising said chlorine dioxide adsorbed in a zeolite, binding said composition to a substrate, adding said composition to a predetermined fluid, applying said composition to a predetermined surface, applying said composition to a predetermined volume, applying an aqueous solution comprising said composition to a predetermined surface, applying an aqueous solution comprising said composition to a predetermined volume, disinfecting via said releasing, decolorizing via said releasing, controlling mildew via said releasing, controlling odor via said releasing, wherein: said composition is in a tablet form, said composition is in a granular form, said composition is in a powder form, said composition is bound to a substrate, and/or said composition is dissolved or dispersed in a fluid.

DEFINITIONS

When the following terms are used substantively herein, the accompanying definitions apply. These terms and definitions are presented without prejudice, and, consistent with the application, the right to redefine these terms via amendment during the prosecution of this application or any application claiming priority hereto is reserved. For the purpose of interpreting a claim of any patent that claims priority hereto, each definition in that patent functions as a clear and unambiguous disavowal of the subject matter outside of that definition.

a—at least one.
acid—a compound capable of neutralizing alkalis and reddening blue litmus paper, containing hydrogen that can be replaced by a metal or an electropositive group to form a salt, or containing an atom that can accept a pair of electrons from a base. Acids are proton donors that yield hydronium ions in water solution, or electron-pair acceptors that combine with electron-pair donors or bases.
activity—an action, act, step, and/or process or portion thereof.
adapted to—made suitable or fit for a specific use or situation.
add—to combine.
adsorb—a process via which zeolites gather and/or accumulate fluids, gasses, liquids, solutes, and/or suspensions, etc.; and/or to gather and/or accumulate fluids, gases, liquids, solutes, and/or suspensions, etc., such as on the surface of another substance, such as a solid.
amount—a quantity.
and/or—either in conjunction with or in alternative to.
apparatus—an appliance or device for a particular purpose
apply—to put to use for a purpose, place in contact with, and/or close physical proximity to and/or to lay and/or spread on.
approximately—about and/or nearly the same as.
aqueous—related to, produced by, similar to, containing, and/or dissolved in water.
at least—not less than.
bind—to adhere, cohere, fasten, secure, hold, and/or constrain; and/or to combine chemically and/or form a chemical bond.
bubble—to flow through and/or to form, produce, and/or emit bubbles
can—is capable of, in at least some embodiments.
cause—to produce an effect.
change—(v.) to cause to be different; (n.) the act, process, and/or result of altering or modifying.
chlorine dioxide—a highly reactive oxide of chlorine with the formula ClO2 or $ClO_2$, it can appear as a reddish-yellow gas that crystallizes as orange crystals at −59° C., and it is a potent and useful oxidizing agent often used in water treatment and/or bleaching.
closed—having boundaries, enclosed.
combine—to join, unite, mix, and/or blend.
complex—an association of compositions, substances, elements, molecules, atoms, and/or ions.
composition of matter—a combination, reaction product, compound, mixture, formulation, material, and/or composite formed by a human and/or automation from two or more substances and/or elements.
compound—composed of two or more substances, parts, elements, and/or ingredients.
comprising—including but not limited to, what follows.
concentration—measure of how much of a given substance there is mixed, dissolved, contained, and/or otherwise present in and/or with another substance.
container—an enclosure adapted to retain a filling and having a closable opening via which a filling can be introduced. Examples of a container include a vial, syringe, bottle, flask, etc.
containing—including but not limited to.
control—to direct.
covalently—characterized by a combination of two or more atoms by sharing electrons so as to achieve chemical stability under the octet rule. Covalent bonds are generally stronger than other bonds.
create—to make, form, produce, generate, bring into being, and/or cause to exist.
deliver—to provide, carry, give forth, and/or emit.
device—a machine, manufacture, and/or collection thereof.
disinfect—to cleanse so as to destroy and/or prevent the growth of disease-carrying microorganisms.
disperse—to cause to separate uniformly throughout a solid, liquid, and/or gas.
dissolve—to make a solution of, as by mixing with a liquid and/or to pass into solution.
dry—(v) to lose and/or remove moisture from; (adj) substantially free from moisture or excess moisture; not moist; not wet.

extract—to separate and/or obtain (a juice, ingredient, etc.) from a mixture by pressure, distillation, treatment with solvents, and/or the like.

fluid—a liquid, slurry, vapor, mist, cloud, plume, and/or foam, etc.

form—(v) to construct, build, generate, and/or create; (n) a phase, structure, and/or appearance.

from—used to indicate a source.

further—in addition.

gas—a state of matter distinguished from the solid and liquid states by relatively low density and viscosity, relatively great expansion and contraction with changes in pressure and temperature, the ability to diffuse readily, and/or the spontaneous tendency to become distributed uniformly throughout any container; and/or a substance in a gaseous state.

gaseous—existing in the state of a gas and/or pertaining to and/or having the characteristics of gas; and/or not solid or liquid.

gel—a fluid ranging in viscosity from a slightly thickened liquid to a semi-solid, often clear or translucent.

granular—any solid substance reduced to a state of relatively coarse, loose particles by crushing, grinding, disintegration, etc.; a substance consisting of ground, pulverized, and/or otherwise relatively coarsely dispersed solid particles; and/or a form characterized by an average particle diameter of greater than approximately 0.5 millimeters and less than approximately 3 millimeters.

greater—larger and/or more than.

having—including but not limited to.

hydrophilic—of, relating to, and/or having a strong affinity for water; and/or tending to dissolve in, mix with, and/or be wetted by water.

hydrophobic—lacking affinity for water; tending to repel and not absorb water; and/or tending not to dissolve in, mix with, and/or be wetted by water.

including—including but not limited to.

initial—at a beginning.

into—to a condition, state, or form of.

introduce—to flow into, over, and/or through, and/or mix with.

may—is allowed and/or permitted to, in at least some embodiments.

method—one or more acts that are performed upon subject matter to be transformed to a different state or thing and/or are tied to a particular apparatus, said one or more acts not a fundamental principal and not pre-empting all uses of a fundamental principal.

mix—to combine (substances, elements, things, etc.) into one mass, collection, or assemblage, generally with a thorough blending of the constituents.

molar ratio—the ratio of moles of one substance to moles of another substance.

non—not.

not—a negation of something.

odor—the property of a substance that activates the sense of smell and/or a sensation perceived by the sense of smell; a scent and/or a disagreeable smell.

percent—one part in one hundred.

plurality—the state of being plural and/or more than one.

polymer—any of numerous natural and synthetic compounds of usually high molecular weight consisting of up to millions of repeated linked units, each a relatively light and simple molecule.

portion—a part, component, section, percentage, ratio, and/or quantity that is less than a larger whole. Can be visually, physically, and/or virtually distinguishable and/or non-distinguishable.

powder—any solid substance reduced to a state of relatively fine, loose particles by crushing, grinding, disintegration, etc.; a substance consisting of ground, pulverized, and/or otherwise relatively finely dispersed solid particles; and/or a form characterized by an average particle diameter of less than approximately 0.5 millimeters.

predetermined—determine, decide, and/or establish in advance.

pressure—a measure of force applied uniformly over a surface.

prior to—before.

recover—to obtain, separate, and/or isolate.

release—to let go and/or free from something that restrains, binds, fastens, and/or holds back.

repeatedly—again and again; repetitively.

result—an outcome and/or consequence of a particular action, operation, and/or course.

retain—to restrain, keep, and/or hold.

said—when used in a system or device claim, an article indicating a subsequent claim term that has been previously introduced.

separate—to disunite, space, set, or keep apart and/or to be positioned intermediate to.

set—a related plurality.

slurry—a relatively thin mixture of a liquid, especially water, and any of several finely divided substances, such as cement, plaster of Paris, coal, and/or clay particles.

solid—neither liquid nor gaseous, but instead of definite shape and/or form.

solution—a substantially homogeneous molecular mixture and/or combination of two or more substances.

solvent—a substance in which another substance is dissolved, forming a solution, and/or a substance, usually a liquid, capable of dissolving another substance.

store—to take in, hold, and/or secure.

stream—a flow of water and/or other fluid substantially—to a great extent or degree.

substrate—an underlying layer.

surface—the outer boundary of an object or a material layer constituting or resembling such a boundary.

system—a collection of mechanisms, devices, machines, articles of manufacture, processes, data, and/or instructions, the collection designed to perform one or more specific functions.

tablet—a small, flat, or flattish cake or piece of some solid or solidified substance temperature—measure of the average kinetic energy of the molecules in a sample of matter, expressed in terms of units or degrees designated on a standard scale.

transform—to change in measurable: form, appearance, nature, and/or character.

treat—to subject to a process, treatment, action, and/or change.

type—a number of things having in common traits or characteristics that distinguish them as a group or class.

utilize—to use and/or put into service.

via—by way of and/or utilizing.

volume—a disk drive and/or virtual disk drive.

wash—to purify (typically a gas and/or gaseous mixture) by passage through and/or over a liquid; and/or to bathe, wet, and/or moisten with water and/or other liquid.

zeolite—any of a group of hydrated silicates of aluminum with alkali metals, either occurring naturally as secondary minerals in cavities in basic volcanic rocks or synthesized, and typically used for their molecular sieve properties because they undergo dehydration with little or no change in crystal structure.

water—a transparent, odorless, tasteless liquid containing approximately 11.188 percent hydrogen and approximately 88.812 percent oxygen, by weight, characterized by the chemical formula $H_2O$, and, at standard pressure (approximately 14.7 psia), freezing at approximately 32° F. or 0 C and boiling at approximately 212° F. or 100 C.

weight—a force with which a body is attracted to Earth or another celestial body, equal to the product of the object's mass and the acceleration of gravity; and/or a factor assigned to a number in a computation, such as in determining an average, to make the number's effect on the computation reflect its importance.

when—at a time.

wherein—in regard to which; and; and/or in addition to.

with respect to—in relation to.

Note

Still other substantially and specifically practical and useful embodiments will become readily apparent to those skilled in this art from reading the above-recited and/or herein-included detailed description and/or drawings of certain exemplary embodiments. It should be understood that numerous variations, modifications, and additional embodiments are possible, and accordingly, all such variations, modifications, and embodiments are to be regarded as being within the scope of this application.

Thus, regardless of the content of any portion (e.g., title, field, background, summary, description, abstract, drawing figure, etc.) of this application, unless clearly specified to the contrary, such as via explicit definition, assertion, or argument, with respect to any claim, whether of this application and/or any claim of any application claiming priority hereto, and whether originally presented or otherwise:

there is no requirement for the inclusion of any particular described or illustrated characteristic, function, activity, or element, any particular sequence of activities, or any particular interrelationship of elements;

any elements can be integrated, segregated, and/or duplicated;

any activity can be repeated, any activity can be performed by multiple entities, and/or any activity can be performed in multiple jurisdictions; and any activity or element can be specifically excluded, the sequence of activities can vary, and/or the interrelationship of elements can vary.

Moreover, when any number or range is described herein, unless clearly stated otherwise, that number or range is approximate. When any range is described herein, unless clearly stated otherwise, that range includes all values therein and all subranges therein. For example, if a range of 1 to 10 is described, that range includes all values therebetween, such as for example, 1.1, 2.5, 3.335, 5, 6.179, 8.9999, etc., and includes all subranges therebetween, such as for example, 1 to 3.65, 2.8 to 8.14, 1.93 to 9, etc.

When any claim element is followed by a drawing element number, that drawing element number is exemplary and non-limiting on claim scope.

Any information in any material (e.g., a United States patent, United States patent application, book, article, etc.) that has been incorporated by reference herein, is only incorporated by reference to the extent that no conflict exists between such information and the other statements and drawings set forth herein. In the event of such conflict, including a conflict that would render invalid any claim seeking priority hereto, then any such conflicting information in such material is specifically not incorporated by reference herein.

Accordingly, every portion (e.g., title, field, background, summary, description, abstract, drawing figure, etc.) of this application, other than the claims themselves (if any), is to be regarded as illustrative in nature, and not as restrictive.

What is claimed is:

1. A composition comprising: chlorine dioxide ($ClO_2$) adsorbed on a ZSM-5 zeolite.

2. The composition of claim 1, further comprising a solvent.

3. The composition of claim 1, further comprising a liquid phase solvent.

4. The composition of claim 1, further comprising a liquid phase aqueous solvent.

5. The composition of claim 1, wherein the chlorine dioxide ($ClO_2$) that is adsorbed on the ZSM-5 zeolite weighs greater than 5 percent of the post-adsorption weight of the ZSM-5 zeolite.

6. The composition of claim 1, wherein the chlorine dioxide ($ClO_2$) that is adsorbed on the ZSM-5 zeolite weighs greater than 10 percent of the post-adsorption weight of the ZSM-5 zeolite.

7. A mixture comprising the composition of claim 1 immersed in a solvent.

8. The mixture of claim 7, wherein the solvent comprises additional chlorine dioxide ($ClO_2$).

9. The mixture of claim 8, wherein the solvent is a liquid phase aqueous solvent and the additional chlorine dioxide ($ClO_2$) is dissolved in the liquid phase aqueous solvent.

10. The mixture of claim 8, wherein (1) the solvent is a liquid phase aqueous solvent, (2) the additional chlorine dioxide ($ClO_2$) is dissolved in the liquid phase aqueous solvent, and (3) the chlorine dioxide ($ClO_2$) that is adsorbed on the ZSM-5 zeolite weighs greater than 5 percent of the post-adsorption weight of the ZSM-5 zeolite.

11. The mixture of claim 8, wherein (1) the solvent is a liquid phase aqueous solvent, (2) the additional chlorine dioxide ($ClO_2$) is dissolved in the liquid phase aqueous solvent, and (3) the chlorine dioxide ($ClO_2$) that is adsorbed on the ZSM-5 zeolite weighs greater than 10 percent of the post-adsorption weight of the ZSM-5 zeolite.

12. The mixture of claim 8, wherein (1) the solvent is a liquid phase aqueous solvent, (2) the additional chlorine dioxide ($ClO_2$) is dissolved in the liquid phase aqueous solvent, (3) the chlorine dioxide ($ClO_2$) that is adsorbed on the ZSM-5 zeolite weighs greater than 10 percent of the post-adsorption weight of the ZSM-5 zeolite, and (4) the chlorine dioxide ($ClO_2$) that is adsorbed on the ZSM-5 zeolite is recoverable via extraction in an amount of 3.0-9.1 percent by post-adsorption weight of the ZSM-5 zeolite.

* * * * *